United States Patent [19]

Foundos et al.

[11] 4,259,867
[45] Apr. 7, 1981

[54] GAS SAMPLE CONDITIONING APPARATUS

[75] Inventors: Albert P. Foundos, Merrick; Roland P. Ricardi, Oceanside, both of N.Y.

[73] Assignee: Fluid Data, Inc., Merrick, N.Y.

[21] Appl. No.: 55,996

[22] Filed: Jul. 9, 1979

[51] Int. Cl.³ ............................................. G01N 1/22
[52] U.S. Cl. ............................................. 73/421.5 R
[58] Field of Search .................. 73/421.5 R, 421.5 A, 73/422 R

[56] References Cited

U.S. PATENT DOCUMENTS 3,675,489  7/1972  Garilli ............................. 73/421.5 R

*Primary Examiner*—S. Clement Swisher
*Attorney, Agent, or Firm*—Weingram & Klauber

[57] ABSTRACT

A gas sample conditioning apparatus is disclosed which is adapted for receiving pyrolysis gases from a hydrocarbon cracking furnace and providing a conditioned gas sample for on-stream process analyzers or the like. The apparatus comprises inlet means for drawing a low velocity flow of the pyrolysis gases from a point downstream of the furnace; a filter reflux and cooling stage overlying and extending upwardly from the inlet means, for accepting the low velocity flow, for filtering and cooling said flow to separate particulate matter and condense undesired hydrocarbon fractions, and for establishing a reflux flow to the inlet to maintain plug-free flow through the stage and to stabilize the temperature gradient therein; a further conditioning stage overlying and extending upwardly from the filter reflux and cooling stage, for accepting the flow proceeding therefrom, the further conditioning stage including a relatively constant temperature section for providing relatively uniform temperature in the flow proceeding from this stage; and outlet means overlying the further conditioning stage for accepting the flow therefrom, and for providing the final output conditioned gas sample.

11 Claims, 7 Drawing Figures

GAS SAMPLE CONDITIONING APPARATUS

BACKGROUND OF INVENTION

This invention relates generally to analytical testing apparatus and the like, and more specifically relates to devices useful in the sampling of gases from hydrocarbon cracking furnaces.

During the operation of hydrocarbon cracking plants and systems, it is necessary to continually withdraw samples of the pyrolysis gases from points downstream of the hydrocarbon cracking furnaces, in order to perform important, if not essential, analytical determinations with respect to the said gases. Thus, for example, it is desirable to continually provide these gases to on-stream process analyzers or the like, in order to establish such important data as the yields of a given hydrocarbon fraction. Further, it may be desired to determine various ratios of gaseous components in the said samples, in order in turn to establish the efficiency with which the cracking system is operating.

In order to carry out the aforementioned operations, the gases which are withdrawn downstream of the cracking furnace, are normally subjected to conditioning apparatus, the purpose of which is to separate from the gross mixture of withdrawn gases, the particular hydrocarbon fraction or fractions which are of interest for furnishing to the analytical instrumentation. In addition to performing a separation of the desired hydrocarbon fractions, particulate matter and the like which may be entrained in the gaseous mixture should be removed, and in other respects the sample rendered at a relatively uniform temperature so that the separated fraction will not vary or change, whereby the results of analysis will be consistent from sample to sample.

In the past, various techniques and apparatus configurations have been utilized for the aforementioned sampling purposes. In one very simple approach, for example, a tube within a tube was inserted into a nozzle in a transfer line proceeding from the cracking furnace. The inner tube contained cold or hot water or steam which continuously poured into the transfer line while gas from the transfer line moved up the outer tube. This technique, however, was extremely troublesome, and required extensive maintenance to keep the sample point operational.

More recently, apparatus has been utilized which improved upon the aforementioned prior art, by employing an internal reflux condenser which is mounted on top of the transfer line, normally in a vertical position but, in some instances, at an angle up to 45°. The internal reflux condenser consists of two sections—a lower packed reflux filter section, and an upper condenser section. Condensables formed in the upper section dropped to the lower reflux section tending to maintain the reflux section in relatively clean condition to limit maintenance requirements. This type of apparatus has been found to provide a relatively good and reliable sample of $C_4$ and lighter hydrocarbons saturated with $C_5$'s and traces of $C_6$'s and heavier fractions. The said apparatus is not, however, practical for use in separating heavier hydrocarbon fraction samples.

In accordance with the foregoing, it may be regarded as an object of the present invention, to provide a gas sample conditioning apparatus adapted for receiving pyrolysis gases from a hydrocarbon cracking furnace, and providing a conditioned gas sample for on-stream process analyzers or the like.

It is a further object of the invention, to provide apparatus of the above character, which is suitable for use in providing conditioned gas samples from a $C_8$ fraction down (i.e. to lower chain length fractions).

It is a yet further object of the invention, to provide apparatus of the foregoing character, which enables sampling from an ethylene or other hydrocarbon cracking furnace transfer line or the like, which operates for long periods without plugging, which maintains a carefully controlled temperature gradient in lower portions of the apparatus in order to achieve accurate separation, and which provides a highly uniform temperature in the sample provided from the said apparatus for testing purposes, thereby assuring relatively maintenance-free operation and good reproduceability of results.

SUMMARY OF INVENTION

Now in accordance with the present invention, the foregoing objects, and others as will become apparent in the course of the ensuing specification, are achieved in a gas sample conditioning apparatus which is adapted for receiving pyrolysis gases from a hydrocarbon cracking furnace and providing a conditioned gas sample for on-stream process analyzers or the like.

The apparatus of the invention comprises inlet means for drawing a low velocity flow of the pyrolysis gases from a point downstream of the furnace; a filter reflux and cooling stage overlying and extending upwardly from the inlet means for accepting the low velocity flow, for filtering and cooling the said flow to separate particulate matter and condense undesired hydrocarbon fraction, and for establishing a reflux flow to the inlet to maintain plug-free flow through the said stage and to stabilize the temperature gradient therein; a further conditioning stage overlying and extending upwardly from the filter reflux and cooling stage, for accepting the flow proceeding therefrom, the further conditioning stage including a relatively constant temperature section providing uniform temperature in the flow proceeding from this stage; and an outlet means overlying the further conditioning stage, for accepting the flow therefrom and for providing the output conditioned gas sample.

The filter reflux and cooling stage of the invention may comprise a lower reflux filter section which is packed with a high surface area packing material, which material filters particulate matter entrained in the low velocity flow, and which enables condensates to form and wet same, to thereby promote reflux to the inlet.

A lower cooling section overlies the reflux filter section, and is provided with cooling means for establishing and maintaining a desired temperature gradient along the flow direction, for condensing moisture and undesired hydrocarbons from the underlying filter section, and for returning same to said lower section to maintain the reflux rate thereat.

A middle packing section overlies and extends upwardly from the lower cooling section, for receiving the gas flow from same, for further filtering and condensing; and for returning condensates and entrained liquids to the lower cooling section.

The said lower cooling section may comprise a plurality of condenser tubes extending from the lower filter section to the middle packing section, together with means for providing a flow of accurately temperature controlled coolant about the tubes, to maintain the desired temperature gradient along the cooling section. The coolant passes from the lower cooling section to an annular cooling space formed about the middle packing section. A temperature sensing means is provided at the middle packing section, which actuates means responsive to the sensed temperature for varying and thereby controlling the temprature of the coolant.

The packing in both the lower and middle packing sections, preferably comprises a porous stainless steel material, such as stainless steel wire or filaments or the like. The packing of the middle section will preferably be denser than that of the packing in the lower section.

The further conditioning stage of the invention preferably comprises an upper cooling section which overlies and extends upwardly from the filter reflux and cooling stage, which section receives the flow from the filter reflux and cooling stage and renders the gases flowing therethrough of relatively uniform temperature. An upper packing section overlies the upper cooling section, and extends upwardly therefrom to the outlet for the apparatus. This section includes a porous packing, which again can be of the stainless steel filamentary or wire type. This section acts to reduce the cross-section of and to coalesce the gas flow to the outlet, and also effects a further degree of filtering.

The upper cooling section may again comprise a plurality of condenser tubes which extends from the filter and reflux stage to the upper packing section, together with means for providing a flow of accurately temperature-controlled coolant about the tubes, to maintain the desired uniformity of temperature. Means are provided for sensing the temperature of the coolant (which also cools the upper packing section), and for maintaining the coolant at the desired relatively constant temperature.

BRIEF DESCRIPTION OF DRAWINGS

The invention is diagrammatically illustrated, by way of example, in the drawings appended hereto, in which.

DESCRIPTION OF PREFERRED EMBODIMENT

Figure 1:
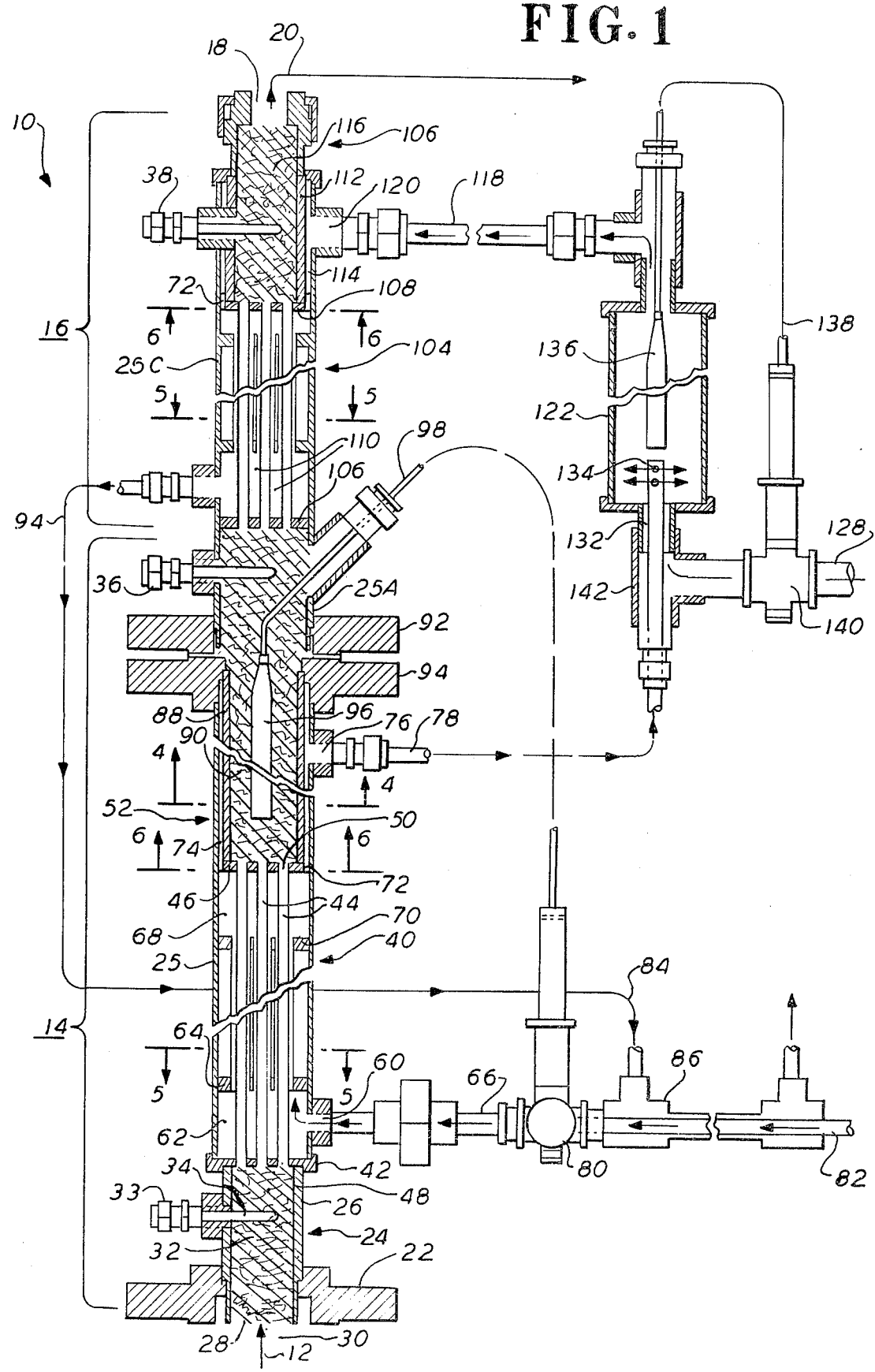
FIG. 1 is a longitudinal cross-sectional view of apparatus in accordance with the present invention. The relationship of certain portions of the apparatus in this Figure, has been expanded for purposes of clarity.

In FIG. 1 herein a longtudinal cross-sectional view appears of apparatus 10 in accordance with the present invention. The view of FIG. 1 may be considered simultaneously with the views of FIGS. 2 and 3 herein, the latter being respectively elevational layout and top plan views which accurately depict the spatial relations of various parts of the apparatus, including especially the relationship of the bulk of the apparatus which appears at the left side of FIG. 1, to the generally parallel branch which appears at the right of FIG. 1 and which includes the temperature regulating means used to maintain uniform temperatures at the upper stage of the apparatus. These relationships will become more evident in the ensuing discussion.

Referring primarily then to FIG. 1, it is seen that the sample conditioning apparatus 10 consists generally of a lower inlet 12, a filter reflux and cooling stage 14 overlying and extending upwardly from inlet 12; a further conditioning stage 16 which overlies and extends upwardly from stage 14; and an outlet 18 from whence the conditioned sample 20 may be provided to on-stream process analyzers or the like.

The inlet 12 is surrounded by a conventional pipe flange 22 which enables connection at the transfer line which proceeds downstream from a conventional hydrocarbon cracking furnace. The latter can be of a conventional type, used e.g. for ethane/propane or naphtha/gas oil cracking or the like. In all instances, the pyrolysis gases to be analyzed are taken downstream from the said furnace, with the apparatus 10 typically being mounted before or after the quench, and thus directly on the process line.

Apparatus 10 will generally be oriented in vertical fashion with respect to the transfer line, in order to promote proper reflux action as will hereinafter be discussed. However, as the term "vertical" is utilized herein, it is to be regarded as including angles which depart up to 45° from a completely vertical line. In all such instances, operation of the device will be fully satisfactory.

Filter reflux and cooling stage 14 consists of three relatively well-defined overlying sections. At the lowermost end of stage 14 there is thus seen to be mounted a lower reflux filter section 24. Section 24 is defined by an outer cylinder 26, which at its lower end passes through flange 22. The lower open end 28 of cylinder 26 provides a large access opening on the transfer line connection, which in turn enables drawing of a low velocity flow of gases 30, which are admitted from the transfer line.

These gases 30, as they proceed into section 24, typically enter same at a flow velocity of the order of 0.3 feet per second. This low flow rate is significant for purposes of the present invention, in that it tends to preclude entrainment of undue quantities of particulate matter, such as solid carbonacous material or large sized liquid droplets or the like, all of which tends to clog or plug the apparatus and especially the packing 32 which is contained within section 24.

Packing 32 preferably comprises a porous compressible stainless steel wire or filamentary material. Typical materials so utilizable are available from Divmet Corporation.

The packing 32 is selected to be sufficiently porous to enable ready passage of the gases proceeding upwardly through section 24. The said material should further, however, have a high surface area in order that it may present a large total surface on which condensate may form, so that in turn the said material will become thoroughly wetted to encourage a reflux, i.e. a recirculation of condensates downwardly to inlet 12, and thus back to the transfer line. This continuous reflux action is of central importance to operation of the present invention, in that the said action assures continuous cleaning of the packing 28 in section 24, thereby preventing any undue buildup of plugs in this portion of the apparatus.

A thermocouple 33 is mounted at one side of section 24, with its probe portion 34 extending into the central regions of packing 32. Thermocouple 33, as well as further thermocouples 36 and 38 which will be further referred to hereinbelow, are not utilized for temperature regulation purposes during operation of the present apparatus; but rather comprise an independent monitoring or checking system for the apparatus. They may typically be used during setup of apparatus 10, in order to check or verify operation of the unit during its use. The temperatures determined by the thermocouples may thus be provided through suitable electrical connections (not shown) to recording and/or monitoring instruments or the like.

Positioned directly in overlying relationship to reflux filter section 24 and extending upwardly therefrom is a lower cooling section 40, which basically comprises a heat exchanger, the operation of which appropriately cools the gases flowing upwardly in apparatus 10 from section 24 so as to condense moisture and undesired hydrocarbons proceeding from the lower filter section 24, and thereupon return these condensates to the lower section 24 to maintain the reflux rate thereat.

Cooling section 40 includes an external wall 25 and is adjoined to cylinder 26 of filter section 24 via a bottom end piece 42. A plurality of condenser tubes 44 extend upwardly from bottom end piece 42 to a top end piece 46 at the uppermost portion of section 40. As may be seen for example, in the cross-sectional view of FIG. 5, these tubes 44 can typically be seven in number. They are open at their lower ends 48, whereby the gases proceeding through section 40 may pass upwardly through the said tubes and after losing various condensates and the like in consequence of passage through same, may exit at the upper ends 50 of same, and thence pass to and through the middle packing section generally designated at 52.

Figure 5:
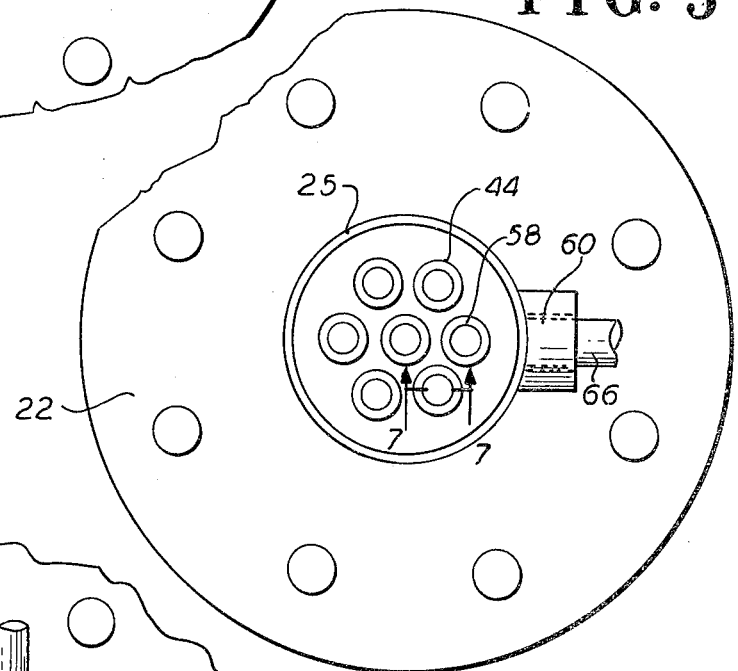
FIG. 5 is a further transverse cross-sectional view of the FIG. 1 apparatus, and is taken along the line 5—5 therein.
Figure 7:
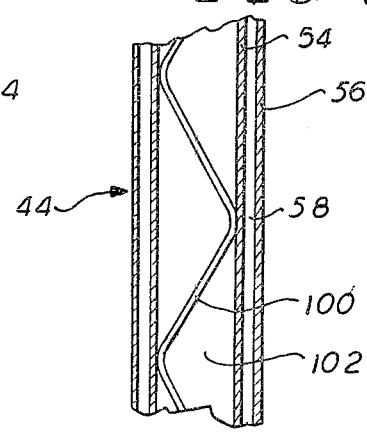
FIG. 7 is a longitudinal cross-sectional view through a fragmentary length of one of the the condenser tubes utilized in the present apparatus, and is taken along the line 7—7 of FIG. 5.

As may be best appreciated from the cross-sectional view of FIG. 5 and from the detailed longitudinal cross-sectional view of FIG. 7, each of the condenser tubes 44 comprises an inner heat conductive cylinder 54, and a spaced outer heat conductive cylinder 56. The space 58 between the two said cylinders provides a passageway for coolant which is provided to the section 40 via a port 60 which opens into a space 62 formed below a cross plate 64 and the aforementioned bottom end piece 42.

Coolant at an appropriate temperature proceeds into port 60 from the line 66. The coolant then passes upwardly from the space 62 through the spaces 58 which surround each of the tubes 44 and exits from these tube spaces into an enlarged space 68, which is defined between an upper plate 70 and the top end piece 46. The coolant thence proceeds through a plurality of openings 72 which are formed in top end piece 46 (see FIG. 6) and thence proceeds through the annular cooling space 74 which is formed about the middle packing section 52, finally exiting from same via the port 76 and the line 78.

The coolant, which proceeds through the cooling section 40 and about section 52, can comprise any suitable fluid, liquid or gaseous in nature; preferably the said coolant comprises air, which is maintained at an appropriate temperature. The temperature of the coolant provided to port 60 is regulated by a temperature control valve 80 which is of conventional construction and may, for example, be of the filled system self-operating type, manufactured by Leslie Co. More specifically, an ambient temperature air supply at a regulated pressure (typically of the order of 50 PSIG) can be provided from line 82 proceeding to valve 80. This ambient temperature air, which proceeds via the line 84 and a connector 86, is used as a heat exchange medium to warm up the incoming coolant.

The hydrocarbon gases proceeding upwardly from lower cooling section 40 thus exit from that section via upper ends 50 of tubes 44 and enter the aforementioned middle packing section 52. Section 52 comprises a cylinder 88, which is spaced from the outer wall 25 to create the aforementioned cooling space 74. Cylinder 88 contains a porous packing 90, which again can be of wire or filamentary type, preferably formed of stainless steel. Packing 90 is preferably denser than the packing 32 at the lower filter section 24. A pair of flanges 92 and 94 hold the upper wall portion 25A to the lower wall portion 25. Wall 25A directly encloses packing 90 at the upper reaches of section 52.

A temperature sensing element is mounted through wall 25A and includes a probe 96 which is centrally contained within the packing material 90. A signal transmission line 98 extends from the probe 96. The temperature sensing element can be of the fluid expansion type, whereby the temperature within packing 90 varies the pressure or volume of fluid contained within probe 96, with the pressure or volume change being transmitted via line 98 to the aforementioned temperature control valve 80 to enable variation in the mixing proportions of the gases proceeding respectively via lines 82 and 84, to thus adjust the temperature of the coolant provided to section 40 (and in turn to section 52).

In accordance with the present invention, it is especially desired to maintain an accurate and uniform temperature gradient from the lower end of cooling section 40 to the upper end thereof, this well-regulated gradient being desirable in order to stabilize the rate of condensation occurring at the interior of condenser tubes 44, to thereby maintain a well-controlled reflux rate, i.e., a return rate of flow of condensates including water vapor, back in a downward direction to the reflux filter section 24—and thence to inlet 12.

The condenser tubes 44 include internal structure facilitating a high and well-controlled rate of condensation and of draining of condensates. In particular, a plurality of internally formed stainless steel wires or ribbons 100 (FIG. 7) are seen to extend longitudinally (in snaked fashion) along the interior space 102 of the tubes 44. These stainless steel ribbons or wires facilitate the formation of condensate and also the flow of condensate in a downward direction once same does form.

Typically, about a minimum 10° C. and a maximum 70° C. drop in temperature is maintained between the bottom and topmost portions of section 40—with the gradient being maintained as uniform as possible along the length of the section.

The middle packing section 52, as previously mentioned, is also seen to include a further thermocouple 36, which serves for use during setup of the apparatus and to check the operation of same. This thermocouple, along with the aforementioned thermocouples 33 and 38, thus as mentioned, provide an independent monitoring or checking system for the present apparatus 10, but do not specifically regulate temperature conditions, such as those of the coolant.

The portions of the apparatus thus far described essentially achieve the hydrocarbon separation of fractions as desired in the instant apparatus, and the removal of any entrained particulate matter or the like. Thus, once the gases proceed above the filter reflux and cooling stage 14, essentially all hydrocarbon separation and removal of particulates has occurred. Above this stage, i.e. at the further conditioning stage 16, additional conditioning is effected—largely intended to render the temperature of the gases which are passed through such further stage at a relatively uniform temperature, and in otherwise stable condition for providing to analytical instrumentation.

The further conditioning stage 16 which overlies and extends upwardly from the filter reflux and cooling stage 24, more specifically adjoining and extending upwardly from middle packing section 52, is seen to comprise two contiguous sections, viz. an upper cooling section 104 which extends from the middle packing section 52, to an upper packing section 106, which overlies section 104. Section 106 extends upwardly to the outlet means 18 of apparatus 10.

Figure 6:
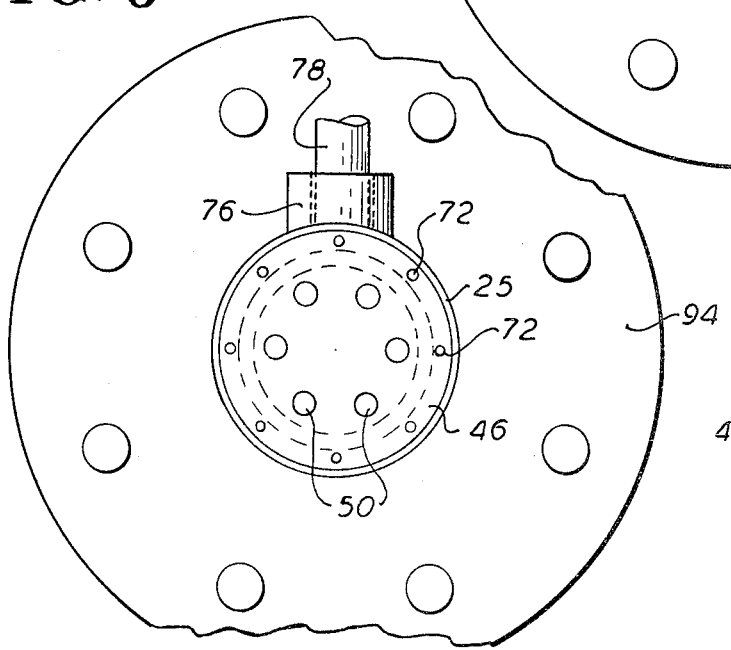
FIG. 6 is a yet further transverse cross-sectional view through the apparatus of FIG. 1, and is taken along the line 6—6 therein.

The structure of upper cooling section 104 precisely parallels that of the lower cooling section 24, as may be directly appreciated from perusal of FIG. 1 and of the cross-sectional views of FIGS. 5 and 6. The said cooling section 104 thus includes a lower end piece 106 and an upper end piece 108, respectively defining the lower and upper ends of the said section. A wall 25C defines the external lateral boundary of section 104; a plurality of condenser tubes 110 extends internally of section 104 between the end pieces 106 and 108.

The said condenser tubes 110, as may be seen again from FIGS. 5 and 6, are structured in accordance with tubes 44, previously described in connection with the lower cooling section 40.

In somewhat analogous fashion to the lower stage 14 of the apparatus 10, the upper packing section 106 directly overlies the upper cooling section 104 and adjoins outlet 18 terminating the apparatus. This upper packing section 106 is defined by a cylinder 112 of metal. Cylinder 112 is spaced from wall 25C to provide an annular cooling space 114. A packing 116 is contained in cylinder 112—this is similar to the packing materials previously described, i.e., it is porous, has high surface and is filamentary or wire-like in nature, and is preferably formed of stainless steel. The packing 116 is preferably of a density similar to packing 90 in section 52.

The upper packing section 106 serves in the present instance not to effect any gross filtering, or to induce any substantial condensation, but rather is intended to coalesce the gas flow proceeding upwardly in apparatus 10, and to reduce the cross-section of the gas flow, with the final controlled and conditioned flow being provided through outlet 18 to analytical instrumentation as aforementioned.

In the instance of further conditioning stage 16, the flow of coolant, which proceeds in the first instance via a line 118, is in a downward direction, exiting stage 16 via the line 84, which as previously mentioned then returns the relatively warm coolant flow to be used as a heat exchange medium with ambient temperature air proceeding via line 82.

The flow of coolant, except for same proceeding in a downward direction, is seen to be similar to the manner in which coolant flows at the stage 14. More specifically, the accurately temperature-controlled coolant proceeding through line 118, enters the upper packing section 104 at port 120 and proceeds about the annular space 114 surrounding cylinder 112 to provide the desired temperature control at the packing section 106. The coolant then proceeds downwardly through openings 72 (see FIG. 6), and thence proceeds downwardly through the annular spacings 58 surrounding each of the tubes 110, in the precise fashion as has been discussed in connection with the flow at lower cooling section 40. Note in this connection that the cross-sectional view through upper cooling section 104 is identical to that through the lower cooling section 40, i.e. in each instance being shown in FIG. 5.

Figure 2:
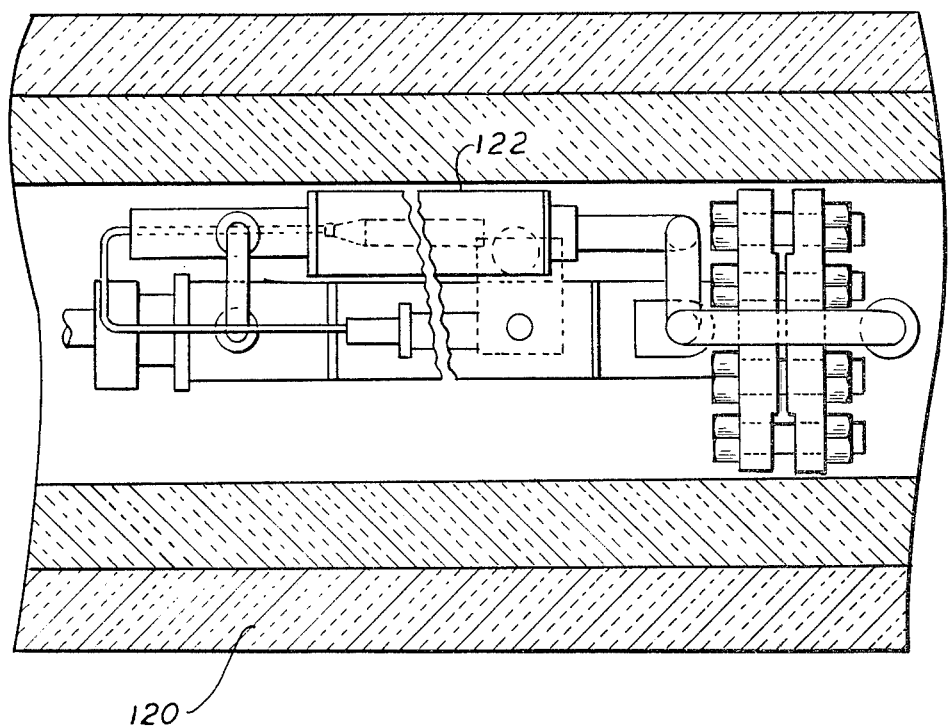
FIG. 2 is a side elevational view, partially sectioned, of the apparatus of the invention, depicting the layout of portions of same in correct size relationship and perspective, the view being taken in the direction 2—2 of FIG. 3.
Figure 3:
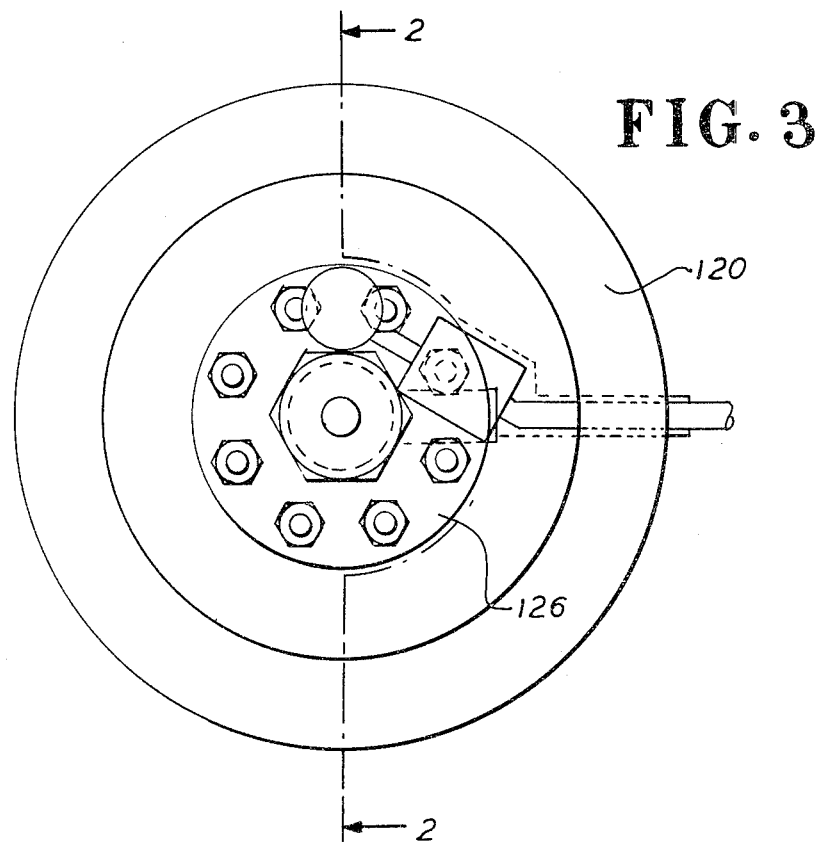
FIG. 3 is a top plan view of the apparatus of the invention.
Figure 4:
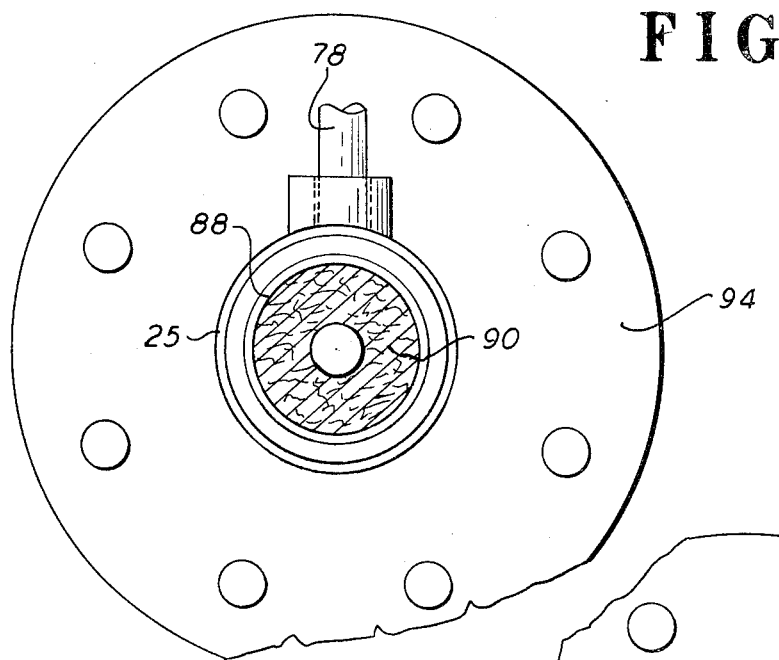
FIG. 4 is a transverse cross-sectional view through the apparatus of FIG. 1, and is taken along the line 4—4 therein.

As aforementioned, the objective in providing cooling at the further conditioning stage 16 is one of maintaining uniform temperature, not of maintaining a temperature gradient. Typically, it is desired that the temperature differential between the lower and uppermost portions of stage 16 not exceed approximately 3° C.

the temperature of the coolant is regulated at an air mixing chamber 122 provided in a line generally running parallel to the portions of apparatus 10 appearing at the left side of FIG. 1. Reference should be made in this connection to FIG. 2 which illustrates the true proximity of the parallel running lines. The distance between these parallel lines has been exaggerated in FIG. 1 for clarity. It will also be seen from FIG. 2 that the entire appratus depicted in FIG. 1 is actually enveloped within a surrounding tube of double-walled insulation 120. Reference may further be had to FIG. 3, showing a top plan view of the apparatus 10; the FIG. 2 view is taken along the line 2—2 of FIG. 3. The surrounding insulation 124 is clearly seen in FIG. 3, as is a top cap 126, which is otherwise removed in the remaining views.

The air mixing chamber 122 receives coolant proceeding from line 78, typically at about 85° C. where the coolant is air. Cold air enters the mixing device via line 128, with hot and cold air flowing parallel at section 124. The air streams then enter chamber 122 via opeing 132 and via ports 134, and the two streams are then thoroughly mixed in chamber 122. A temperature sensing element 136 extends into the chamber 122. This element 36 can be of the liquid-filled variety. The control line 138 from same, actuates a conventional temperature control valve 140, which varies the amount of cold air provided from line 128. The thoroughly mixed and regulated coolant, as aforementioned, is then provided from line 118 to further conditioning stage 16, where it effects its desired accurate temperature control of the latter.

While the present invention has been particularly set forth in terms of specific embodiments thereof, it will be understood in view of the instant disclosure, that numerous variations upon the invention are now enabled to those skilled in the art, without yet departing from the teaching of the invention. Accordingly, the invention is to be broadly construed, and limited only by the scope and spirit of the claims now appended hereto.

I claim:

1. A gas sample conditioning apparatus for receiving pyrolysis gases from a hydrocarbon cracking furnace and providing a conditioned gas sample for on-stream process analyzers or the like said apparatus comprising:

inlet means for drawing a low velocity flow of said pyrolysis gases from a point downstream of said furnace;

a filer reflux and cooling stage overlying and extending upwardly from said inlet means, for accepting said low velocity gas flow, for filtering and cooling said flow to separate particulate matter and condense undesired hydrocarbon fractions, and for establishing a reflux flow to said inlet to maintain plug-free flow through said stage and to stabilize the temperature gradient therein; said filter reflux and cooling stage comprising a lower reflux filter section which is packed with a porous high surface area packing, said packing filtering said particulate matter entrained in said low velocity gas flow, and enabling condensates to form and wet the packing to thereby enable and promote said reflux to said inlet; a lower cooling section overlying said reflux filter section, said section being provided with cooling means for maintaining a desired temperature gradient along the gas flow direction, for condensing moisture and undesired hydrocarbons in the gas flow proceeding from said lower filter section, and for returning the resulting condensates to said lower section to maintain the reflux rate thereat; and a middle packing section overlying and extending upwardly from said lower cooling section, for receiving the gas flow from same, a porous packing being contained in said section for returning further flow to said lower cooling section;

a further conditioning stage overlying and extending upwardly from said filter reflux and cooling stage, for accepting the gas flow proceeding therefrom, said conditioning stage including a relatively constant temperature section for maintaining uniform temperature in the flow proceeding from said stage; and outlet means overlying said further conditioning stage, for accepting the gas flow therefrom, and for providing said conditioned output gas sample from said apparatus.

2. Apparatus in accordance with claim 1, wherein said filter reflux and cooling stage comprises:
  a lower reflux filter section which is packed with a porous high surface area packing, said packing filtering said particulate matter entrained in said low velocity gas flow, and enabling condensates to form and wet the packing to thereby enable and promote said reflux to said inlet;
  a lower cooling section overlying said reflux filter section, said section being provided with cooling means for maintaining a desired temperature gradient along the gas flow direction, for condensing moisture and undesired hydrocarbons in the gas flow proceeding from said lower filter section, and for returning the resulting condensates to said lower section to maintain the reflux rate thereat; and
  a middle packing section overlying and extending upwardly from said lower cooling section, for receiving the gas flow from same, a porous packing being contained in said section for returning further flow to said lower cooling section.

3. Apparatus in accordance with claim 2, wherein said lower cooling section comprises a plurality of condenser tubes extending from said lower reflux filter section to said middle packing section; and means for providing a flow of accurately temperature-controlled coolant about said tubes, to maintain said desired temperature gradient along said cooling section.

4. Apparatus in accordance with claim 2, wherein said condenser tubes include wires snaking longitudinally along the interiors thereof, for facilitating formation of condensates and draining of same.

5. Apparatus in accordance with claim 3, wherein said coolant is further circulated about said middle packing section; said apparatus including a temperature sensing means at said middle packing section, and means responsive to the sensed temperature for varying the temperature of said coolant.

6. Apparatus in accordance with claim 5, wherein the packing of said lower cooling section comprises stainless steel.

7. Apparatus in accordance with claim 6, wherein the packing of said middle packing section comprises stainless steel, and is of greater density than the said packing at said lower reflux filter section.

8. A gas sample conditioning apparatus for receiving pyrolysis gases from a hydrocarbon cracking furnace and providing a conditioned gas sample for on-stream processes analyzers or the like; said apparatus comprising:
  inlet means for drawing a low velocity flow of said pyrolysis gases from a point downstream of said furnace;
  a filter reflux and cooling stage overlying and extending upwardly from said inlet means, for accpeting said low velocity gas flow, for filtering and cooling said flow to separate particulate matter and condense undesired hydrocarbon fractions, and for establishing a reflux flow to said inlet to maintain plug-free through said stage and to stabilize the temperature gradient therein;
  a further conditioning stage overlying and extending upwardly from said filter reflux and cooling stage, for accepting the gas flow proceeding therefrom, said conditioning stage including a relatively constant temperature section for maintaining uniform temperature in the flow proceeding from said stage; said further conditioning stage comprising an upper cooling section overlying and extending upwardly from said filter reflux and cooling stage, for receiving the gas flow from said reflux and cooling stage, said cooling section being adapted for rendering the gases flowing therethrough of relatively uniform temperature; and an upper packing section ovelying said upper cooling section and extending upwardly therefrom to said outlet means, said upper packing section including a porous packing for coalescing the gas flow to said outlet; and
  outlet means overlying said further conditioning stage, for accepting the gas flow therefrom, and for providing said conditioned output gas sample from said apparatus.

9. Apparatus in accordance with claim 8, wherein said upper cooling section comprises a plurality of condenser tubes extending from said filter and reflux stage to said upper packing section; and means for providing a controlled flow of accurately temperature-controlled coolant about said tubes to maintain said desired uniform temperature throughout said upper cooling section.

10. Apparatus in accordance with claim 9, wherein said condenser tubes include wires snaking longitudinally along the interiors thereof, for facilitating formation of condensates and draining of same.

11. Apparatus in accordance with claim 9, wherein said coolant is further circulated about said upper packing section; said apparatus including means for sensing the temperature of said coolant circulating to said further conditioning stage, and for maintaining said coolant at a relatively constant temperature throughout said further conditioning stage.

* * * * *